United States Patent [19]
Smith et al.

[11] Patent Number: 6,110,710
[45] Date of Patent: Aug. 29, 2000

[54] SEQUENCE MODIFICATION OF OLIGONUCLEOTIDE PRIMERS TO MANIPULATE NON-TEMPLATED NUCLEOTIDE ADDITION

[75] Inventors: Jeffrey R. Smith; John D. Carpten, both of Derwood; Michael J. Brownstein, Rockville, all of Md.

[73] Assignee: The United States of America as represented by the Secretary of the Department of Health and Human Services, Washington, D.C.

[21] Appl. No.: 09/051,620

[22] PCT Filed: Oct. 15, 1996

[86] PCT No.: PCT/US96/16544

§ 371 Date: Jun. 15, 1998

§ 102(e) Date: Jun. 15, 1998

[87] PCT Pub. No.: WO97/16566

PCT Pub. Date: May 9, 1997

[51] Int. Cl.[7] ................ C12P 19/34; C12Q 1/68
[52] U.S. Cl. .................. 435/91.2; 435/6
[58] Field of Search ............. 435/6, 91.2

[56] References Cited

U.S. PATENT DOCUMENTS

| | | | |
|---|---|---|---|
| 4,683,195 | 7/1987 | Mullis et al. | 435/6 |
| 5,008,182 | 4/1991 | Sninsky et al. | 435/5 |
| 5,411,876 | 5/1995 | Bloch et al. | 435/91.2 |
| 5,451,505 | 9/1995 | Dollinger | 435/6 |

OTHER PUBLICATIONS

Clark et al. Nucleic Acid Res. 16(20):9677–9686, Nov. 1988.

Gengxi Hu, DNA polymerase–catalyzed addition of non-templated extra nucleotides to the 3' end of a DNA fragment, DNA and Cell Biology 12(8):763–770 (Oct. 1993).

Jeffrey R. Smith, et al., "Approach to genotyping errors caused by nontemplated nucleotide addition by Taq DNA polymerase," Genome Research, pp. 312–317, (Jul. 18, 1995).

Michael J. Brownstein, et al., "Short technical reports," BioTechniques, 20(6):1004–1010.

*Primary Examiner*—Eggerton A. Campbell
*Attorney, Agent, or Firm*—Townsend and Townsend and Crew LLP

[57] ABSTRACT

The present invention is directed to methods for resisting or promoting template independent nucleotide addition to the 3' terminus of a DNA duplex. The process comprises amplifying a target nucleic acid using primers which comprise a 5' terminal sequence which resists or promotes non-templated nucleotide addition to the 3' terminus of the complementary nucleic acid strand. The invention is also directed to a kit for cloning 3' nucleotidylated duplex DNA.

25 Claims, 2 Drawing Sheets

SEQUENCE MODIFICATION OF OLIGONUCLEOTIDE PRIMERS TO MANIPULATE NON-TEMPLATED NUCLEOTIDE ADDITION

BACKGROUND OF THE INVENTION

The impact of the polymerase chain reaction (PCR) on biological research is perhaps most clearly evidenced by the number and variety of specific applications of this technique. The power and versatility of PCR amplification has transformed this method into a standard tool in molecular biology research and created an ever increasing demand for PCR instrumentation and reagents. An unfortunate corollary of PCR is that errors resulting from properties inherent to the reagents are amplified and unwittingly interpreted as the target sequence.

One prevalent source of error is DNA polymerase catalyzed non-templated addition of a nucleotide to the 3' hydroxyl terminus of duplex PCR products. This activity has been reported for DNA polymerases from *Thermus aquaticus*, polymerase α from chick embryo, rat polymerase β, reverse transcriptase from avian myeloblastosis virus, and DNA polymerase I from *Saccharomyces cerevisiae*. Clark, *Nucleic Acids Research*, 16(20):9677–9686 (1988). In the presence of all four deoxynucleotidetriphosphates (dNTPs), these DNA polymerases differ in the efficiency with which particular dNTPs are added but generally display a preference for non-templated addition of dATP. Clark reported that template independent addition required a duplex DNA substrate but stated that adenylation cannot involve the use of coding information from the template strand. More recently, it was reported that Taq polymerase is relatively resistant to adding an extra nucleotide on a 3' terminal adenosine, and relatively efficient at adding an adenosine residue on a 3' terminal cytosine. Hu, *DNA and Cell Biology*, 12(8):763–770 (1993).

At best, non-templated 3' adenylation of an otherwise blunt-ended duplex may result in inefficient cloning. More disturbing, however, is its impact on genotyping, where artifactual variations in marker size may adversely impact interpretations of family relationships, medical diagnosis, and forensics. Moreover, full automation of genotyping has been hampered by the necessity of manually editing collected data to correct for allele misidentification due to the unpredictability of non-templated nucleotide addition.

What is needed in the art is a means to control (i.e., reduce or more consistently promote) non-templated nucleotide addition. Further, a method to facilitate template independent addition is needed to exploit the advantageous properties of 3' adenylated PCR products. Quite surprisingly, the subject invention provides these and other advantages.

SUMMARY OF THE INVENTION

The present invention relates to a method of promoting a non-templated 3' adenosine addition to a PCR amplification product. The method comprises the steps of amplifying a target with a primer comprising the 5' terminal sequence 5'-G-T-K-N-3' wherein K is G or T/U, N is A, C, G, or T/U and wherein at least one of said terminal sequence residues is not complementary to the target sequence. In one embodiment, the 5' terminal sequence is 5'-G-T-K-N-V-N-N-3' wherein V is A, C, or G. In another embodiment, the 5' terminal sequence is 5'-G-T-K-T-V-N-N-3'. In a preferred embodiment, the 5' terminal sequence is 5'-G-T-T-T-V-N-N-3'. Typically, adenosine addition is catalyzed by a thermostable DNA polymerase such as Taq polymerase.

In another aspect, the present invention relates to a method of resisting non-templated 3' adenosine addition to a PCR amplification product. The method comprises the steps of amplifying a target with a primer comprising the 5' terminal sequence 5'-Y-M-V-3' wherein Y is C or T/U, M is A or C, V is A, C, or G, and wherein at least one of said terminal sequence residues is not complementary to the target strand. In a preferred embodiment, the 5' terminal sequence is 5'-Y-M-V-V-N-N-N-3' wherein N is A, C, G, or T/U. In preferred embodiments, the primer is linked at the 5' terminus to an adenylation inhibiting group such as biotin or primary amine.

In a further aspect of the present invention, primers comprising 5' terminal sequences for promoting or resisting template independent nucleotide addition may be used independently of one another to create duplex DNA products with 0, 1, or 2 3' adenylated overhangs. Duplex DNA products comprising an adenylated 3' overhang can be cloned into a vector comprising an overhang with a 3' thymidine. In yet another aspect, the present invention relates to kits for performing the methods of the present invention.

The present invention has utility as a method of producing adenylated PCR products which can be readily cloned into thymidylated vectors. The present method permits cloning of PCR products in a desired orientation. The present invention also has utility in ensuring consistent marker sizes in, for example, genotyping.

DETAILED DESCRIPTION OF THE INVENTION

Figure 1:
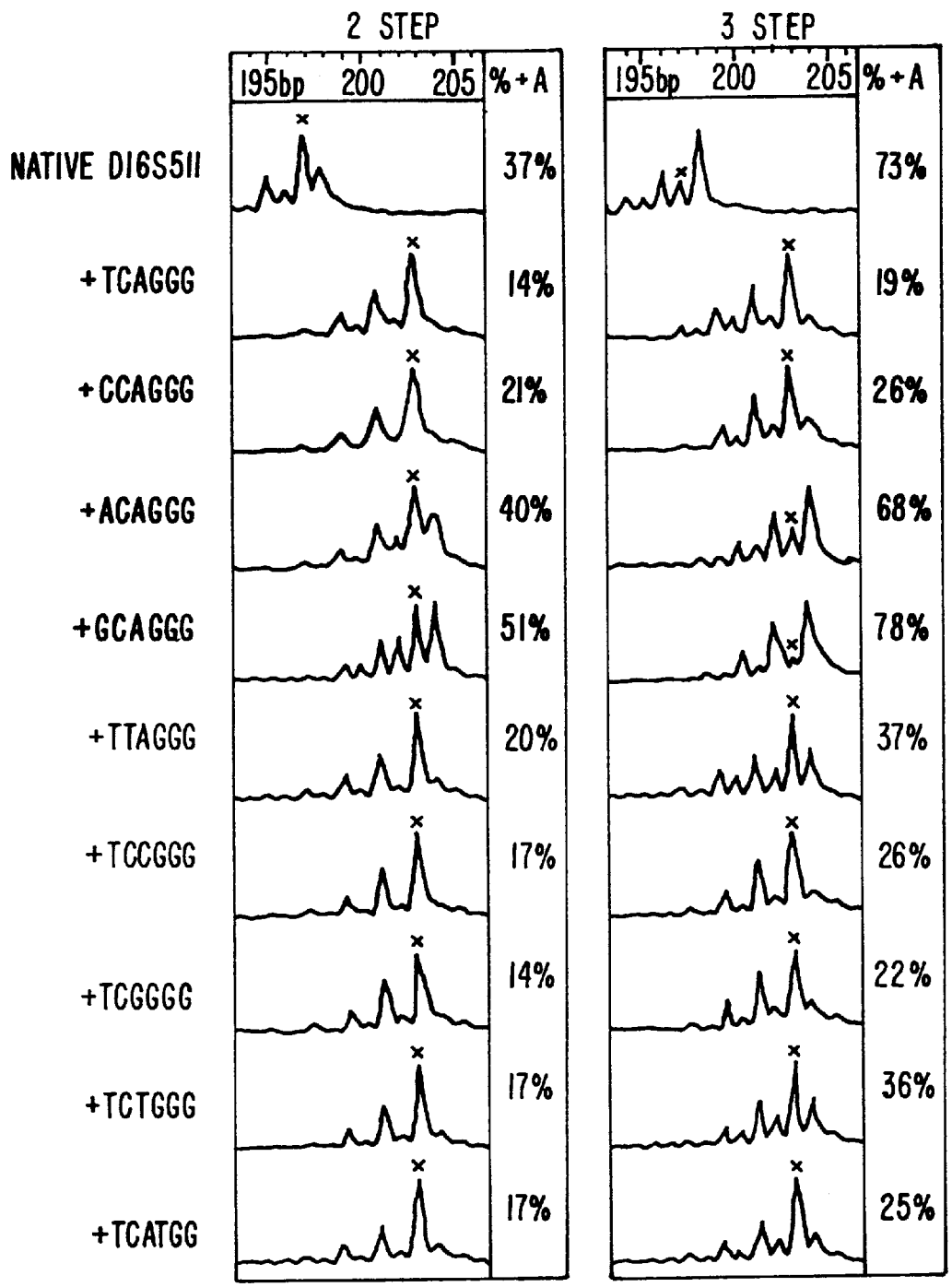
FIG. 1 shows primer modifications that resist formation of non-template adenylated products. Percent +A (non-template adenylated) was calculated by dividing the height of the +A peak by the sum of the heights of the true (non-adenylated) and +A peaks.

The terms "non-templated 3' nucleotide addition," "non-templated addition," "template independent addition" or "blunt-end addition" as used herein, refer to the DNA polymerase catalyzed formation of a phosphodiester bond between a nucleotide and a 3' hydroxyl terminus of a blunt-end nucleic acid duplex without base-pairing to a template strand. Such addition results in the formation of 3' nucleotide overhang on said blunt-end nucleic acid duplex.

The term "primer" as used herein, refers to an oligonucleotide whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxynucleotide. The primer must be sufficiently long to prime the synthesis of extension products in the presence of the agent for polymerization. The exact lengths of the primers will depend on many factors, including temperature and source of primer. For example, depending on the complexity of the target sequence, the oligonucleotide primer typically contains 15–25 or more nucleotides, although it may contain fewer nucleotides. Short primer molecules generally require cooler temperatures to form sufficiently stable hybrid complexes with template.

The primers herein are selected to be "substantially" complementary to a region of the target sequence which is to be amplified. This means that the primers must be able to hybridize (i.e., "anneal") with the target under conditions that permit primer extension. Therefore, the primer sequences need not reflect the exact sequence of the target sequence to which they anneal. For example, a non-complementary nucleotide fragment may be attached to the 5' end of the primer to act as a "tail", with the remainder of the primer sequence being perfectly or substantially complementary so as to anneal to the target strand. Alternatively, non-complementary bases or longer sequences can be interspersed into the primer, provided that the primer sequence has sufficient complementarity with the sequence of the target strand to be amplified to hybridize therewith and thereby permit synthesis of the extension product.

Primers may be "forward" or "reverse." A forward primer refers to the primer used to initiate synthesis of the strand in which the primer is incorporated. A reverse primer refers to the primer used to initiate synthesis of the strand which is complementary to the strand whose synthesis was initiated by the forward primer.

The term "oligonucleotide," as used herein is defined as a molecule comprised of two or more deoxyribonucleotides or ribonucleotides.

The term "template," as used herein, refers to the nucleic acid strand which serves as the model for the synthesis of the "anti-template" or complementary strand as dictated by base pairing. Typically, the template is at least 50 to 100 nucleotides in length, and preferably at least 100 to 200 nucleotides in length.

The term "target," as used herein, refers to the starting nucleic acid in the amplification process which is to be amplified in whole or part.

The term "terminal sequence," as used herein, refers to the nucleic acid sequence located at the 5' or 3' end (i.e., terminus) of a linear nucleic acid sequence.

The term "PCR amplification product," as used herein, refers to a nucleic acid duplex of complementary strands and two blunt-ends (i.e., without 5' or 3' overhangs), formed as a result of the PCR reaction.

The term, "hybridization," as used herein, refers to the formation of a duplex nucleic acid, under conditions conducive to the pairing of complementary bases of the individual nucleic acid strands.

The term, "thermostable DNA polymerase," as used herein, refers to a DNA polymerase which retains substantial polymerization activity at the elevated temperature conditions of the PCR. Typically, thermostable DNA polymerases, or engineered derivatives thereof, are isolated from thermophilic bacteria such as *Thermus aquaticus*.

As used herein, "adenylation inhibiting group" includes reference to a chemical group which, when linked covalently or non-covalently to an amplification primer, increases the percentage of true product (i.e., reduces the percentage of non-template adenylated product). Adenylation inhibiting groups cause at least a 5% increase in the percentage of true product when the target is amplified using a 2-step PCR protocol, as described in Example 1 and 2, in the presence of an equimolar solution of the nucleoside triphosphates, dATP, dCTP, dGTP, dTTP.

The present invention relates to methods and kits for promoting or resisting a 3' non-templated addition to a PCR amplification product. The present invention may be used to obtain greater consistency in the sequence and length of PCR products, or to facilitate cloning into complementary 3' modified vectors. Methods of PCR amplification are well known to those of skill in the art and disclosed, inter alia, in U.S. Pat. Nos. 4,683,195 and 5,411,876.

The present invention involves the use of primers which comprise 5' terminal sequences for promoting or resisting non-templated nucleotide addition to the 3' end of the complementary strand of a PCR amplification product. The 5' terminal sequences of primers of the present invention may be chosen so that each nucleotide can base pair (i.e., is complementary) with the opposing nucleotides of the target nucleic acid, or they may be, in whole or part, a non-annealed tail of the primer. Thus, a tail may comprise 0, 1, 2, 3, 4, 5, 6, 7 or more nucleotides of the 5' terminal sequences of the present invention.

Primers of the present invention that resist non-templated nucleotide addition to the complementary strand comprise a 5' terminus having the sequence 5'-Y-M-V-3', preferably, 5'-Y-M-V-V-3', and most preferably 5'-Y-M-V-V-N-N-N-3' where Y is C, T or U, M is A or C, V is A, C, or G, and N is A, C, G, T or U. Nucleotide analogs well known to the skilled artisan may also be used. For example, deoxyinosine may be used to provide the base at each of the N positions of the 5' terminal sequence. Primers of the present invention promoting non-templated nucleotide addition to the complementary strand comprise a 5' terminus having the sequence 5'-G-T-K-N-3' wherein K is G or T/U, and N is A, C, G, T or U, preferably, 5'-G-T-K-N-V-3' where V is A, C, or G, more preferably, 5'-G-T-K-N-V-N-N-3', and most preferably 5'-G-T-T-T-V-N-N-3'. Nucleotide analogs, (e.g, deoxyinosine to provide the base in place of N) can be substituted for the standard nucleotides, preferably at or 3' to the third position of the 5' terminal sequence for promoting template independent addition.

An adenylation inhibiting group can be linked to the 5' terminus of the 5' terminal sequence. The adenylation inhibiting group allows amplification of the target nucleic acid sequence while reducing the percentage of amplification product which is modified by non-templated addition. Thus the adenylation inhibiting group increases the percentage of true product. The increase in the percentage of true product is conveniently determined using the 2-step PCR protocol as described in Example 1 and 2, in the presence of an equimolar solution of the nucleoside triphosphates, dATP, dCTP, dGTP, dTTP. Typically the increase in true product is by at least 5%, more preferably at least 10%, frequently by at least 15%, and most preferably at least 20% relative to a control lacking the adenylation inhibiting group. Those of skill will recognize that adenylation inhibiting groups are selected to be compatible with primers for use in PCR amplification procedures. Adenylation inhibiting groups include chemiluminescent or fluorochrome dyes, labels, and linking groups such as biotin, or derivatives thereof. Preferably, the adenylation inhibiting group is biotin or a primary amine. The adenylation inhibiting group may be linked covalently or non-covalently to the 5' terminus of the 5' terminal sequence via a chain not exceeding about 20 covalent bonds in length, usually by no more than 15, preferably by no more than 12 covalent bonds in length, and most preferably by no more than 6 or 3 covalent bonds in length. The adenylation inhibiting group has a molecular weight of between 200 and 500 daltons.

The primer 5' terminal sequences for resisting or promoting non-templated nucleotide addition may be used independently of one another in the PCR. Consequently, primers may be chosen to yield PCR amplification products with 0, 1 or 2 non-templated 3' nucleotide additions (i.e., 0, 1 or 2 3' overhangs). Primers may also be modified by e.g., subtraction, addition, insertion or deletion to fit the 5'terminal sequences of the present invention by methods well known to those of skill in the art. For example, to fit the 5' terminal sequences of the present invention, 1, 2, 3, 4, or more nucleotides may be added to the 5' terminus of a primer.

Without being bound by theory, it is believed that the efficiency with which a particular nucleotide is added in a template independent fashion is primarily dependent upon the particular DNA polymerase used. Generally, in the presence of an equimolar solution of all four nucleoside triphosphates, adenosine is added most efficiently. However, increasing, decreasing, or eliminating one or more of the four nucleotides from the PCR reaction mixture may be used to alter the incorporation frequency of template independent addition. Typically, the nucleotides employed will be deoxyribonucleotides (e.g., dATP, dGTP, dCTP, dTTP, dITP) or analogs thereof such as deoxythioribonucleotides or 7-deaza-dGTP. However, dideoxyribonucleotides or analogs thereof may be used at the conclusion of a primer extension cycle of the PCR to effect a template independent dideoxynucleotidyl addition. Nucleotides may be labelled using methods and compositions well known to the skilled artisan.

Generally, the 5' terminal sequences of primers employed for resisting non-templated nucleotide addition will result in less than 30% to 40% of PCR amplification products with complementary strands modified by non-templated addition, preferably less than 20% to 30% modified by non-templated addition. 5' terminal sequences of the primers employed for promoting non-templated nucleotide addition will result in at least 65% to 70% of PCR amplification with complementary strands modified by non-templated addition, preferably at least 75% to 80% modified by non-templated addition. The DNA polymerase chosen to catalyze template independent addition may be chosen from those displaying such activity, such as DNA polymerases from *Thermus aquaticus*, polymerase α from chick embryo, rat polymerase β, reverse transcriptase from avian myeloblastosis virus, and DNA polymerase I from *Saccharomyces cerevisiae* or *E. coli*. Preferably, the DNA polymerase will be thermostable. A particularly preferred thermostable DNA polymerase is Taq polymerase or genetically engineered or chemically derivatized versions thereof.

In one aspect of the present invention, a PCR amplification product with each terminus having a 3' adenosine addition is formed using both primers having 5' terminal sequences promoting template independent 3' addition. This PCR product can be cloned into a deoxy- or dideoxythymidine tailed vector wherein a single thymidine 3' overhang is available at each 3' end. Exemplary methods of constructing such "T-tailed" vectors are disclosed by Holton et al., *Nucleic Acids Research*, 19(5):1156 (1990); Kovalic et al., *Nucleic Acids Research*, 19(16):4560 (1991); and Marchuk et al., *Nucleic Acids Research*, 19(5):1154 (1990). Alternatively, a vector that is completely T-tailed may be produced by linearizing a plasmid containing the palindromic sequence 5'AAGACAC/GTGTCTT3' and inserting it into the plasmid of one's choice. Cutting the above plasmid with the restriction enzyme BbrPI (Boehringer Mannheim), or an isoschizomer thereof (e.g., Pml I) at the site indicated yields a blunt-ended product with a 3' terminus that should readily be thymidylated. A single thymidine at each 3' terminus is readily achieved using conventional methods as described by, e.g., Holton et al. or Marchuk et al.

In another aspect of the present invention, a PCR amplification product with one 3' blunt-end addition is formed using one 5' terminal sequence resisting template independent nucleotide addition and one 5' terminal sequence promoting template independent nucleotide addition. The single 3'overhang permits the duplex to be cloned in the desired orientation (i.e., directionally cloned) into a vector with a complementary 3' overhang. Such vectors can be produced by, for example, incorporating a Xcm I restriction site into a standard polylinker to generate 3' thymidine overhangs as taught by, e.g., Kovalic et al. Either terminus can be blunt-ended using the appropriate restriction enzyme to yield a vector into which the PCR amplification product can be directly cloned in the desired orientation.

Although the present invention has been described in some detail by way of illustration and example for purposes of clarity of understanding, it will be obvious that certain changes and modifications may be practiced within the scope of the appended claims.

EXAMPLE I

This Example describes the elucidation of the 5' terminal sequences for resisting or promoting template independent nucleotide addition.

All PCR reactions were carried out using 60 ng of template DNA (CEPH individuals 884-01, -02, -03, or -04 (BIOS Laboratories, New Haven, Conn.). Fifteen microliter reaction volumes contained 50 mM potassium chloride, 1.5 mM magnesium chloride, 10 mM Tris-HCl pH 8.3, 333 nM each forward and reverse primer, 0.6 units of AmpliTaq DNA polymerase (Perkin-Elmer, Norwalk, Conn.), and 250 $\mu$M each DNTP (dATP, dCTP, dGTP, dTTP). Fluorescently labeled (6-Fam, Hex, or Tet) forward primers of human dinucleotide repeat markers were obtained from Applied Biosystems/Perkin-Elmer (Foster City, Calif.) or Research Genetics (Huntsville, Ala.). These were used with reverse primers from the same sources or with tailed reverse primers synthesized on a CYCLONE PLUS DNA synthesizer (MilliGen/Biosearch, Burlington, Mass.). The primers were purified according to the method of Sawadogo and Van Dyke (*Nucleic Acids Research* 19:67 (1991)) and two consecutive butanol precipitations were performed. The markers studied are listed in Table 1.

Three PCR protocols were employed using Perkin-Elmer model 9600 thermocyclers (Perkin-Elmer, Norwalk, Conn.).

A. 2 step. 95° C. for 5 minutes followed by 10 cycles of 94° C. for 15 seconds, 55° C. for 15 seconds, followed by an additional 23 cycles of 89° C. for 15 seconds, 55° C. for 15 seconds. Total time: 1 hour and 8 minutes. This protocol favors production of "true" products (i.e., template independent non-adenylated products).

B. 2 step/30 minute final extension. As above followed by a 30 minute final extension at 72° C.

C. 3 step/10 minute final extension. 95° C. for 5 minutes followed by 10 cycles of 94° C. for 15 seconds, 55° C. for 15 seconds, 72° C. for 30 seconds, followed by an additional 20 cycles of 89° C. for 15 seconds, 55° C. for 15 seconds, 72° C. for 30 seconds, followed by a final extension at 72° C. for 10 minutes. Total time: 1 hour and 30 minutes. This protocol favors the generation of "plus A" products (i.e., template independent adenylated products).

The native (untailed) or modified (tailed) markers were used independently to amplify products from single DNA targets, and the 15 μl reaction products were diluted to 100 μl with water. Then 1.5 μl of each product was mixed with 2.5 μl formamide, 0.5 μl blue dextran loading dye, and 0.5 μl internal size standard GS-500 (Applied Biosystems/ Perkin-Elmer, Foster City, Calif.). The size standard contains DNA fragments fluorescently labeled with the dye phosphoramidite TAMRA (red) ranging in size from 50 to 500 base pairs. After heat denaturation at 95° C. for 5 minutes, the tubes were chilled on ice.

Two different Applied Biosystems DNA sequencers were employed—a model 373A and a model 377. For the model 373, 3.5 μl of the PCR product/size standard mix was electrophoresed in one lane of a 7% denaturing polyacrylamide gel (BioRad, Hercules, Calif.) at 15 W constant power (12 cm well-to-read, filter set B). For the model 377, 2.5 μl of the mix were electrophoresed in one lane of a 5% denaturing polyacrylamide gel at 3000 V constant voltage, 2400 scans per hour (36 cm well-to-read). Fluorescently labeled DNA fragments were analyzed using ABI GENES-CAN 672 (Ver.1.2.2-1) software on the model 373, and ABI GENESCAN (Ver. 2.0.1 fc2) and ABI Prism 377 (Ver 1.1) Collection software on the model 377. Genotype data were generated using ABI GENOTYPER (Ver1.1r8) DNA fragment analysis software.

Two primers were chosen having opposite properties: D4S398 and D16S511. About 15% of the PCR product of marker D4S398 is plus A modified (i.e., template independent adenylated) when either protocol A or C is used. Marker D16S511, on the other hand, yields products that are roughly 40% and 75% plus A, respectively, when these protocols are employed. When the three (TCA), four (TCAA), five (TCAAT), or six (TCAATT) bases comprising the 5' end of the reverse primer of marker of D4S398 were added to the 5' end of the D16S511 reverse primer, there was a progressive decrease in product adenylation using protocol C from 75% for the native marker to 43%, 41%, 39%, and 33% for the three, four, five, and six base-tailed primers respectively. The optimal sequence was sought by progressively substituting bases at each of the six positions of the tail. The results are illustrated in FIG. 1 wherein asterisks indicate the true (non-adenylated) products. The top electrophoretogram shows that marker D16S511 generates non-adenylated 197 bp (63%) and adenylated 198 bp (37%) products when it is amplified using a 2 step PCR protocol (A) which does not favor adenylation. Using a 3 step protocol followed by a 10 minute final extension (C), 73% of the product is adenylated. Addition of TCAGGG to the 5' end of the reverse primer of marker D16S511 dramatically changes its performance. The 203 bp product generated resists adenylation, even when protocol C is employed. Replacing the T in position 1 of the tail by G, A, or C (in order of potency) causes a reduction in its ability to protect from adenylation. Similarly, substitutions of T for C in position 2, T for A in position 3, or T for G in position 4 cause some deterioration in the performance of the tail.

A weak consensus emerged for the sequence that resists adenylation: 5' T (or C, but not A or G); A or C; A, C or G; A, C, or G; N; N 3' (N=A, C, G, or T). While the base chosen for positions 5 and 6 seemed to have little impact, the length of the tail was important. Six or seven bases were required for best activity. TCACAC, TCAGGG (see FIG. 1), TAACTG, and TAACTGG were chosen as sequences representative of the consensus and these tails were added to each of the markers listed in Table 1.

TABLE 1

| Marker | Reverse Primer 5' Sequence | % Adenylation 2 step PCR | % Adenylation 3 step + 10 PCR | % Adenylation Average |
| --- | --- | --- | --- | --- |
| D1S199 | CAAAGAC | 4 | 25 | 14 |
| D16S405 | TGAAGGC | 12 | 33 | 22 |
| D4S398 | TCAATT | 15 | 15 | 15 |
| D15S131 | TTAAAAA | 24 | 29 | 26 |
| D15S127 | AACAGTT | 25 | 65 | 45 |
| D1S207 | GCAAGTC | 42 | 64 | 53 |
| D10S197 | GTGATAC | 50 | 66 | 58 |
| D5S436 | GTCTCCA | 61 | 66 | 63 |
| D16S511 | CAGCCCA | 45 | 80 | 62 |
| D8S279 | GTGTCAG | 66 | 78 | 72 |
| D1S255 | GTGATGG | 57 | 92 | 75 |
| D5S406 | GGGATGC | 64 | 90 | 76 |
| D6S276 | GGGTGCA | 71 | 86 | 78 |
| D13S173 | GTCTCTG | 75 | 82 | 78 |

The reverse primers of the markers listed in this table were modified as previously described. Percent adenylation of the "native" markers was calculated as in FIG. 1. The figures given are means of several amplifications, while the figures in the last column are averages of the values in the preceding two columns. Percent adenylation of products that are not modified or products that are heavily modified are fairly consistent from amplification to amplification regardless of target. All the tails markedly inhibited adenylation of the PCR products, but none was universally effective. In general, markers that were strongly modified to plus A when the native reverse primer was used were most resistant to the action of the tail. This suggests that Taq polymerase interacts with a stretch of base pairs longer than the six or seven encoded by the tails.

Figure 2:
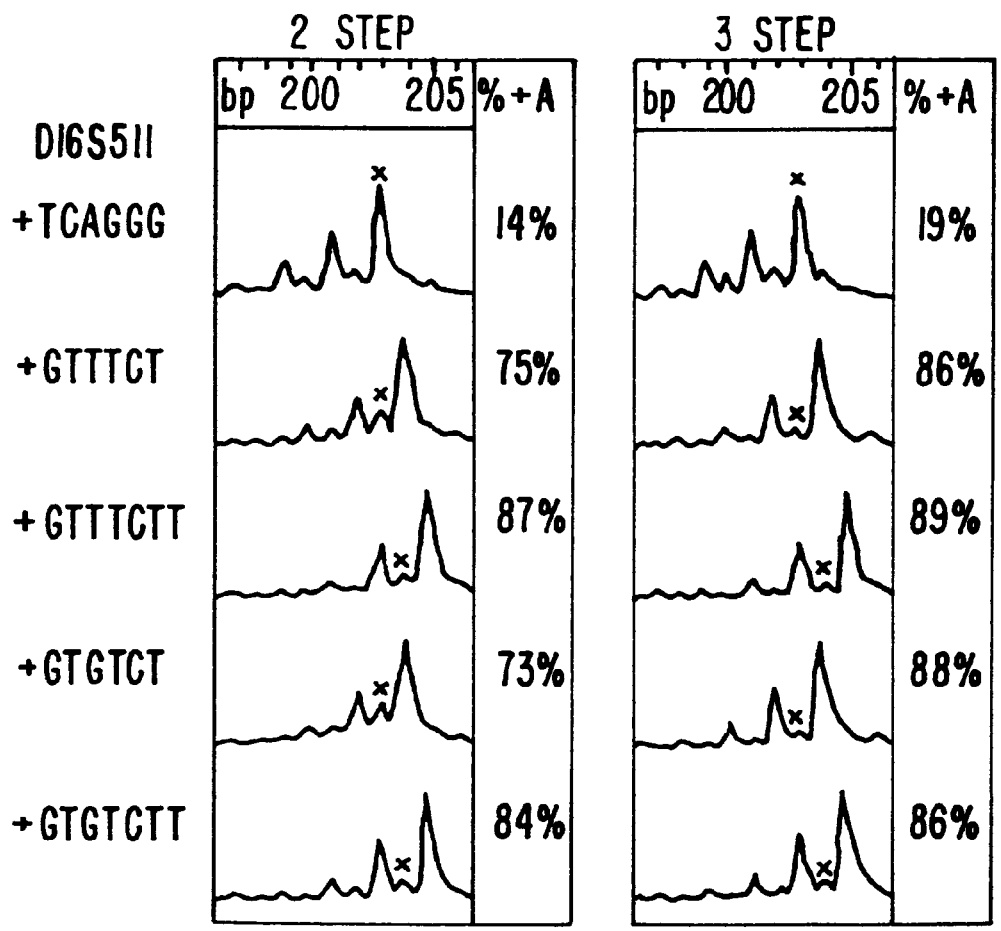
FIG. 2 shows primer modifications that strongly promote non-template adenylation. Percent +A was calculated as described in FIG. 1.

Tails that would consistently have the opposite effect were also sought. The products of the last six markers in Table 1 could be predicted to be heavily adenylated based on the findings summarized above. In designing a plus A modifying tail, a G was placed on the 5' end because of the observation that this favors adenylation (FIG. 1). A T was placed in positions 2, 3, and 4 because it was found in the studies summarized above that this also favors adenylation (FIG. 1). The 5' sequences of the last six primers in Table 1 fit the design quite well. On the basis of these sequences, it was decided on GTTTCT as a reasonable tail to test. Addition of this tail to the reverse primers of the markers listed in Table 1 resulted in nearly complete adenylation of each one when they were amplified using thermocycling protocols A, B, or C. An example of this effect is shown in FIG. 2 where asterisks indicate the non-adenylated products. Addition of GTTTCT or GTTTCTT to the reverse primer of marker D16S511 has just the opposite effect from addition of TCAGGG. The TCAGGG-tailed primer generates a 203 bp non-adenylated product. GTTTCT- and GTTTCTT-tailed primers generate 204 bp and 205 bp adenylated products, respectively, even when the PCR conditions used do not favor non-templated addition of nucleotide; substitution of G for T in the third position of the tail has little effect on its performance. As mentioned earlier, adding a seventh, arbitrarily chosen, base to the tail improves its performance somewhat. This spacer may somehow buffer the tail from the effects of internal sequences.

It was not necessary to add the entire six or seven base tail to all reverse primers. Certain primers (e.g., the last five in Table 1) can be used as is. Other primers can be modified to fit the following consensus: 5' G; T; T; T; (A, C, or G) 3'. Add GTTT to reverse primers with A, C, or G on their 5' ends;

add GTT to primers starting with T followed by A, C, or G; add GT to primers ending with TT followed by A, C, or G. When the primers listed in Table 1 were modified according to this scheme, they generated products that were greater than 85% adenylated using PCR protocols B or C. The products were more than 70% adenylated when protocol A, the protocol of choice for rapid throughput genotyping, was used.

Over 50 markers have been modified with the plus A consensus tail. All yielded predominantly adenylated products readily identified by the GENOTYPER software. As stated above, there is no need routinely to add a 6 or 7 base tail to the reverse primer to promote adenylation, but product yield sometimes increases when the reverse primer has a 6 base tail.

EXAMPLE II

This Example describes the effect on non-templated addition by groups added to the 5'-terminus of PCR primers.

PCR reactions were carried out using 60 ng of template DNA (CEPH individuals 884-15 and 884-05, BIOS Laboratories, New Haven, Conn.). Fifteen microliter reaction volumes contained 50 mM potassium chloride, 1.5 mM magnesium chloride, 10 mM Tris-HCl pH8.3, 333 nM each forward and reverse primer, 0.6 units of AmpliTaq DNA polymerase (Perkin-Elmer, Norwalk, Conn.), and 250 µM each dNTP (dATP, dCTP, dGTP, dTTP). Fluorescently labeled (6-FAM, HEX, or TET) forward primers of human dinucleotide repeat markers were obtained from Applied Biosystems/Perkin-Elmer (Foster City, Calif.). These were used with "native" reverse primers from the same source or modified reverse primers synthesized on a CYCLONE PLUS DNA synthesizer (MilliGen/Biosearch, Burlington, Mass.), or purchased from Research Genetics (Huntsville, Ala.) or Genosys (The Woodlands, Tex.). 5'-acetyl, -amino, -biotin, -DIG (digoxigenin), -HEX (4, 7, 2',4',5',7'-hexachloro-6-carboxy-fluorescein), and -thiol modified primers were tested. The 5' modifying groups were linked via a carbon backbone of three to six carbons in length. The primers were desalted prior to use. The markers studied included, D5s427, D11s937, D13s325, D14s80, D16s511, and D20s95.

Two PCR protcols were employed using Perkin-Elmer model 9600 thermocyclers (Perkin-Elmer, Norwalk, Conn.):

A. 2 step. 95° C. for 5 minutes followed by 10 cycles of 94° C. for 15 seconds, 55° C. for 15 seconds, followed by an additional 23 cycles of 89° C. for 15 seconds, 55° C. for 15 seconds.

B. 3 step/10 minute final extension. 95° C. for 5 minutes followed by 10 cycles of 94° C. for 15 seconds, 55° C. for 15 seconds, 72° C. for 30 seconds, followed by an additional 20 cycles of 89° C. for 15 seconds, 55° C. for 15 seconds, 72° C. for 30 seconds, followed by a final extension at 72° C. for 10 minutes.

Native (unmodified by a 5' terminal sequence) or modified markers were used independently to amplify single DNA targets, and the 15 µl reaction products were diluted to 100 µl with water. Then 1.5 µl of each product was mixed with 2.5 µl formamide, 0.5 µl blue dextran loading dye, and 0.5 µl internal size standard GS-500 (Applied Biosystems/Perkin-Elmer, Foster City, Calif.). After heat denaturation at 95° C. for 5 minutes, the tubes were chilled on ice.

An Applied Biosystems model 373 DNA sequencer was used to characterize the PCR products. Three and one half microliters of the PCR product/size standard mix was electrophoresed in one lane of a 7% denaturing polyacrylamide gel (BioRad, Hercules, Calif.) at 15 W constant power (12 cm well-to-read, filter set B). Fluorescently labeled DNA fragments were analyzed using ABI Genescan 672 (Ver. 1.2.2-1). Genotype data were generated using ABI GENOTYPER (Ver. 1.1r8) DNA fragment analysis software. Results are summarized in Table II and III.

TABLE II

| | Percent True (2 step PCR protocol) | | Percent True (3 Step PCR protocol) | |
|---|---|---|---|---|
| Marker | Native reverse primer | Biotinylated primer | Native reverse primer | Biotinylated primer |
| D1s207 | 70.0 | 86.5 | | |
| D6s276 | 66.7 | 75.8 | | |
| D16s511 | 58.5 | 78.0 | 37 | 54 |
| D5s406 | 53.6 | 76.9 | | |
| D10s197 | 50.0 | 83.3 | | |
| D13s173 | 17.8 | 56.5 | | |

Table II demonstrates that markers with native primers which generate products that are 50–70% true (i.e., 30–50% +A) are all aided by addition of biotin; when the 2 step PCR protocol is used more than 76% of the product is true.

D13s173 is a marker that strongly prefers to be adenylated, even when the 2 step PCR protocol is employed. However, Table II shows the strength of the effect of biotin. Additional experiments demonstrate that an amino modification is a less effective adenylation inhibiting group than biotin. Using identical 2 step PCR conditions, biotin produced about a 20% decrease in the percentage of adenylation of D16s511 while the amino modification produced a 12% decrease.

TABLE III

Marker D13s173 (% True)

| Native PCR Condition | Native | Native + Biotin | True Tail | True Tail + Biotin |
|---|---|---|---|---|
| 2 STEP | 17.8 | 56.5 | 75.3 | 81.2 |
| 3 STEP | 7.8 | 32.5 | 71.6 | 75.1 |
| 3 STEP + 30' | 5.9 | 15.2 | 64.1 | 68.9 |

Table III shows the effect on non-templated 3' adenylation of marker D13s173 by: a biotinylated native primer, 2- vs. 3-step PCR protcol, use of a primer having a 5' terminal sequence that favors the true product, and prolonged (30 min.) final extension time. As indicated, adding a 5' terminal sequence (TCAGGGC (SEQ ID NO:)) that inhibits non-templated 3' adenosine addition to D13s173 inhibits adenylation; adding biotin further reduces the level of adenylation. Additional experiments demonstrate that adding an amino modification to the 5' end of the reverse primer of D16s511 had an effect that was similar to, but not as pronounced as, that seen with biotin. No effect was observed when 5'-acetyl, DIG, HEX, or -thiol modified primers were tested.

In sum, the results demonstrate that biotin used in concert with a 5' terminal sequence that protects against adenylation ensures that nearly 100% of the product will be the "true" allele vs the +A product. Finally, it appears that biotinylated markers usually generate significantly more product than unmodified ones.

All publications and patents mentioned in this specification are herein incorporated by reference into the specification to the same extent as if each individual publication or patent was specifically and individually indicated to be incorporated herein by reference.

What is claimed is:

1. A method of promoting a non-templated 3' adenosine addition to a PCR amplification product, comprising:
amplifying a target with a primer having a 5' terminal sequence 5'-G-T-K-T-3' wherein K is G or T/U and N is A, C, G, T, or U and wherein at least one of said terminal sequence residues is not base paired to the target sequence.

2. A method of resisting a non-templated 3' adenosine addition to a PCR amplification product, comprising:
amplifying a target with a primer having a 5' terminal sequence 5'-Y-M-V-3' wherein Y is C or T/U, M is A or C, V is A, C, or G, and wherein at least one of said terminal sequence residues is not base-paired to the target strand.

3. The method of claim 1, wherein said adenosine addition is catalyzed by a thermostable DNA polymerase.

4. The method of claim 3, wherein said thermostable DNA polymerase is Taq polymerase.

5. The method of claim 1, wherein the primer for target amplification comprises the 5' terminal sequence 5'-G-T-K-T-3'.

6. The method of claim 2, wherein each primer for target amplification comprises the 5' terminal sequence 5'-Y-M-V-3'.

7. The method of claim 2, wherein a primer for target amplification comprises the 5' terminal sequence 5'-Y-M-V-3' to form said PCR amplification product without a single 3' adenylated overhang.

8. The method of claim 1, wherein said 5' terminal sequence is 5'-G-T-K-N-V-N-N-3' wherein V is A, C, or G.

9. The method of claim 2, wherein said 5' terminal sequence is 5'-Y-M-V-V-N-N-3' wherein N is A, C, G, T or U.

10. The method of claim 1, wherein each nucleotide of said 5' terminal sequence is not complementary to the target strand.

11. The method of claim 2, wherein each nucleotide of said 5' terminal sequence is not complementary to the target strand.

12. The method of claim 1, wherein amplification is performed for at least 10 cycles wherein each cycle is initially at about 89° C. for approximately 15 seconds, then about 55° C. for approximately 15 seconds and finally about 72° C. for approximately 30 seconds.

13. The method of claim 2, wherein amplification is performed for at least 10 cycles wherein each cycle is initially at about 89° C. for approximately 15 seconds, then about 55° C. for approximately 15 seconds.

14. The method of claim 8, wherein said 5' terminal sequence is 5'-G-T-T-T-C-N-N-3'.

15. The method of claim 14, wherein said 5' terminal sequence is 5'-G-T-T-T-C-T-T-3'.

16. The method of claim 1, wherein said 5' terminal sequence is 5'-G-T-G-T-C-N-N-3'.

17. The method of claim 7 for directional cloning, wherein said PCR amplification product is cloned into a vector comprising a blunt end and a single thymidine 3' overhang.

18. The method of claim 1, wherein said duplex PCR product is cloned into a vector comprising two single thymidine 3' overhangs.

19. The method of claim 2, wherein said target amplification is catalyzed by a thermostable DNA polymerase.

20. The method of claim 19, wherein said thermostable DNA polymerase is Taq polymerase.

21. A kit for performing the method of claim 7, comprising primers with the 5' terminal sequences of 5'-Y-M-V-3' and 5'-G-T-K-N-3'.

22. A kit for performing the method of claim 5, comprising primers with the 5' terminal sequence 5'-G-T-K-T-3'.

23. The method of claim 2, wherein the primer is linked at the 5' terminus to an adenylation inhibiting group.

24. The method of claim 23, where the adenylation inhibiting group is biotin or primary amine.

25. The method of claim 1 wherein a primer for target amplification comprises the 5' terminal sequences 5'-G-T-K-N-3' wherein K is G or T/U and N is A, C, G, T or U to form said PCR amplification product with a 3' adenylated overhang.

* * * * *

UNITED STATES PATENT AND TRADEMARK OFFICE
CERTIFICATE OF CORRECTION

PATENT NO. : 6,110,710
DATED : Aug. 29, 2000
INVENTOR(S) : Smith et al.

It is certified that error appears in the above-identified patent and that said Letters Patent is hereby corrected as shown below:

IN THE CLAIMS:

In column 11, claim 1, line 8, delete "5'-G-T-K-T-3'" and insert therefor --5'-G-T-K-N-3'--.

Signed and Sealed this

Fifteenth Day of May, 2001

NICHOLAS P. GODICI

Attest:

Attesting Officer

Acting Director of the United States Patent and Trademark Office